United States Patent
Chen

(10) Patent No.: US 10,376,560 B2
(45) Date of Patent: Aug. 13, 2019

(54) AQUEOUS SOLUTION FORMULATIONS OF VANCOMYCIN

(71) Applicant: LATITUDE PHARMACEUTICALS, INC., San Diego, CA (US)

(72) Inventor: Andrew Xian Chen, San Diego, CA (US)

(73) Assignee: LATITUDE PHARMACEUTICALS, INC., San Diego, CA (US)

(*) Notice: Subject to any disclaimer, the term of this patent is extended or adjusted under 35 U.S.C. 154(b) by 0 days.

(21) Appl. No.: 15/649,284

(22) Filed: Jul. 13, 2017

(65) Prior Publication Data

US 2017/0304396 A1 Oct. 26, 2017

Related U.S. Application Data

(63) Continuation of application No. PCT/US2016/016829, filed on Feb. 5, 2016.

(60) Provisional application No. 62/113,322, filed on Feb. 6, 2015.

(51) Int. Cl.
| | |
|---|---|
| *A61K 9/00* | (2006.01) |
| *A61K 9/08* | (2006.01) |
| *A61K 38/14* | (2006.01) |
| *A61K 47/02* | (2006.01) |
| *A61K 47/18* | (2017.01) |
| *A61K 47/22* | (2006.01) |
| *A61K 31/405* | (2006.01) |
| *A61K 31/7028* | (2006.01) |

(52) U.S. Cl.
CPC ............ *A61K 38/14* (2013.01); *A61K 9/0019* (2013.01); *A61K 9/08* (2013.01); *A61K 31/405* (2013.01); *A61K 31/7028* (2013.01); *A61K 47/02* (2013.01); *A61K 47/183* (2013.01); *A61K 47/22* (2013.01)

(58) Field of Classification Search
CPC .... A61K 31/7028; A61K 47/02; A61K 38/14; A61K 47/183; A61K 9/08; A61K 47/22; A61K 31/405; A61K 9/0019; A61K 2300/00
See application file for complete search history.

(56) References Cited

U.S. PATENT DOCUMENTS

| | | | | |
|---|---|---|---|---|
| 4,421,741 A | * | 12/1983 | Gilbert | .................. A61K 9/0048 514/12.2 |
| 4,670,258 A | | 6/1987 | Harris et al. | |
| 2003/0092622 A1 | | 5/2003 | Sato et al. | |
| 2008/0160555 A1 | * | 7/2008 | Rambach | .................. C12Q 1/04 435/19 |
| 2011/0300097 A1 | * | 12/2011 | Al-Qahtani | .......... A61K 9/0048 424/85.2 |
| 2014/0079777 A1 | | 3/2014 | Lord et al. | |

FOREIGN PATENT DOCUMENTS

| WO | WO 1997/019690 A1 | 6/1997 |
|---|---|---|
| WO | 2014/085526 A1 | 6/2014 |

OTHER PUBLICATIONS

Sanchez et al, D-Amino Acids Enhance the Activity of Antimicrobials against Biofilms of Clinical Wound Isolates of *Staphylococcus aureus* and Pseudomonas aeruginosa, Antimicrobial Agents and Chemotherapy, 2014, 58, pp. 4353-4361.*
Xing et al, Molecular Interactions between Glycopeptide Vancomycin and Bacterial Cell Wall Peptide Analogues, Chem. Eur. J., 2011, 17, pp. 14170-14177.*
Carmen et al, Ultrasonically Enhanced Vancomycin Activity Against *Staphylococcus epidermidis* Biofilms In Vivo, Journal of Biomaterials Applications, 2004, 18, pp. 237-245.*
Kolodkin-Gal et al, d-Amino Acids Trigger Biofilnn Disassembly, Science, 2010, 328, pp. 627-629.*
Izutsu, Stabilization of Therapeutic Proteins by Chemical and Physical Methods, from Therapeutic proteins, methods and protocols, Humana press, edited by C. Mark Smales and David C. James, 2005, pp. 287-292.*
Slama et al, Temperature and Solute Molecular Size Effects on the Retention and Enantioselectivity of a Series of D, L Dansyl Amino Acids on a Vancomycin-Based Chiral Stationary Phase, Chromatographia, 2003, 58, pp. 399-404.*
Vancomycin, from https://pubchem.ncbi.nlm.nih.gov/compound/vancomycin#section=Top, p. 1, accessed Dec. 19, 2018.*
Tryptophan, from https://pubchem.ncbi.nlm.nih.gov/compound/L-tryptophan, p. 1, accessed Dec. 19, 2018.*
Aqueous Solution Definition in Chemistry, from https://www.thoughtco.com/definition-of-aqueous-solution-604370?print, May 14, 2017, pp. 1-2.*
Mueller Hinton Broth, from HiMedia Laboratories, Feb. 2015, pp. 1-2.*
ISA/US; International Search Report dated May 16, 2016 in PCT/US2016/016829.
EP Patent Application No. 16 74 7356; Supplementary European Search Report, dated Aug. 28, 2018, 3 pages.

* cited by examiner

*Primary Examiner* — Karlheinz R. Skowronek
*Assistant Examiner* — Li N Komatsu
(74) *Attorney, Agent, or Firm* — Kilpatrick Townsend & Stockton LLP

(57) ABSTRACT

This invention relates to aqueous solution compositions of vancomycin that are stable, ready for use and do not require reconstitution.

15 Claims, 4 Drawing Sheets

The structure of vancomycin

Rearrangement of vancomycin to the
degradation products CDP-1-M and CDP-1-m

AQUEOUS SOLUTION FORMULATIONS OF VANCOMYCIN

CROSS-REFERENCE TO RELATED APPLICATIONS

This application is a continuation of International Application No. PCT/US2016/016829, filed Feb. 5, 2016, which application claims priority to U.S. Application No. 62/113,322, filed Feb. 6, 2015, the disclosures of which are hereby incorporated by reference in their entireties for all purposes.

FIELD OF THE INVENTION

This invention relates to solution compositions comprising vancomycin, tryptophan and water, which are useful for the treatment and prevention of infections.

BACKGROUND OF THE INVENTION

Vancomycin is an important antibiotic, often prescribed for the treatment of staphylococcal infections or other infections caused by gram-positive bacteria, particularly methicillin-resistant strains of *staphylococcus* (MRSA). Vancomycin (FIG. 1) degrades in water to a number of products including its predominant degradation products, which are known as vancomycin CDP-1, or CDP-1-M and CDP-1-m (collectively, the CDP-1s) (see Sheldrick et. al., Nature 271:223, 1978, Harris et. al., J. Am. Chem. Sci. 1983, 105, 6915-6922). CDP-1 formation relates to hydrolysis, deamidation and re-arrangement of an asparagine moiety in the vancomycin structure (FIG. 2). CDP-1s are insoluble in water and readily precipitate from solution, rendering the solution unsafe for injection. Although the vancomycin degradation pathways and structures of CDP-1s are well elucidated, there is no available method for inhibiting the CDP-1 formation in water or vancomycin degradation in general. To date, a liquid, aqueous and ready-to-use vancomycin drug product is not available because of the limited stability of vancomycin in water.

Currently, vancomycin is formulated for pharmaceutical use as a dry powder in capsules for oral administration, and as a sterile dry powder filled in vials or as a frozen liquid preparation for parenteral use. The dry powder filled in vials is produced by lyophilization and must be dissolved in water before it can be injected. The frozen liquid needs to be thawed and warmed to room temperature before use. Both forms are costly to manufacture, distribute and store and inconvenient because they are not in ready-to-use formats. Therefore, an aqueous and ready-to-use vancomycin solution formulation is highly desirable. A solution formulation will have reduced manufacturing costs by eliminating the need for lyophilization. Pharmacy time and labor and their costs could be reduced because there will be no need to reconstitute the dry powder nor will there be the need for freezer storage.

A solution prepared from the currently marketed product (i.e. a reconstituted solution from the vancomycin dry powder or a thawed solution from the frozen solution) would fail the impurity and/or particulate matter specifications, as defined by the United States Pharmacopeia for Vancomycin Injection, USP, for in a matter of hours or few days due to the rapid generation of CDP-1s. The formation of CDP-1s is the shelf-life-limiting degradation pathway for vancomycin in water.

Therefore, a solution formulation in which vancomycin is stabilized is desirable. Furthermore, such a stable vancomycin solution formulation enables the development of other dosage forms of vancomycin for topical, ophthalmic, otic, intranasal, instillation or intravaginal routes of administration for use in applications where a ready-to-use solution is typically required.

WO 1997019690 A1 discloses stable solutions of vancomycin hydrochloride comprising between about 0.5% and about 12% w/v vancomycin hydrochloride and between about 0.5% and about 30% v/v ethanol. These solutions are particularly useful for storage in a liquid state not requiring either freezing or freeze drying in order to maintain stability of the active agent. There is no mention of using tryptophan as a stabilizer for vancomycin in this patent.

WO 2014085526 A1 teaches a stabilized, lipid-based glycopeptide antibiotic composition comprising: (a) a lipid component; (b) a glycopeptide antibiotic component; and (c) an amino acid or a derivative thereof, wherein the amino acid or the derivative thereof stabilizes the glycopeptide antibiotic. Exemplary amino acids and amino acid derivatives suitable for the invention include alanine (ALA), D-alanine (D-ALA), alanine-alanine (ALA-ALA), beta-alanine (bALA), alanine-beta-alanine (ALA-bALA), 3-aminobutanoic acid (3-ABA), gamma-aminobutyric acid (GABA), glutamic acid (GLU or GLUt), D-glutamic acid (D-GLU), glycine (GLY), glycylglycine (GLY-GLY), glycine-alanine (GLY-ALA), alanine-glycine (ALA-GLY), aspartic acid (ASP), D-aspartic acid (D-ASP), lysine-alanine-alanine (LYS-ALA-ALA), L~Lysine-D~alanine-D~alanine (L-LYS-D-ALA-D-ALA), lycine, tricine, sarcosine, and iminodiacetic acid (IDAA). There is no mention of using tryptophan as a stabilizer for vancomycin in this patent.

WO 2012159103 A1 discloses a composition comprising vancomycin or a pharmaceutically acceptable salt thereof, wherein the composition is a dry powder, and wherein the composition further comprising a hydrophobic amino acid selected from the group consisting of: tryptophan, tyrosine, leucine, trileucine, and phenylalanine. The inventors stated, "It may be desirable to include a hydrophobic amino acid in a composition of the present disclosure so as to improve the physical stability and/or dispersibility of the composition, improve the chemical stability of vancomycin or a pharmaceutically acceptable salt thereof, and/or to alter the taste of the composition by masking the bitter taste of vancomycin and its salts, and/or to alter the rate the composition is absorbed into the systemic circulation from the lung (e.g., increase or slow the rate). While not wishing to be bound to any particular theory, it is currently believed that the hydrophobic amino acid additive remains on the surface of the particles and protects them from moisture and light, thereby increasing the stability of the formulation." There is no teaching or suggestion in this patent to use tryptophan as a stabilizer for vancomycin in solution to inhibit CDP-1 formation.

US 20070116649 A1 patent application discloses an aqueous or powder composition that contains an anti-gram-positive antibiotic or salt thereof being present at a concentration ranging from about 0.6 to about 0.9 of the water solubility limit at 25° C. and 1.0 atmosphere, of the anti-gram-positive antibiotic or salt thereof. The anti-gram-positive antibiotics include vancomycin and exemplary excipients as bulking agents, buffers or dispersing agents include hydrophobic amino acids such as leucine, valine, isoleucine, tryptophan, alanine, methionine, phenylalanine, tyrosine, histidine, and proline. According to Merck Index ($12^{th}$ edition), the solubility of vancomycin hydrochloride in water is >10% w/v, therefore, the vancomycin concentration range from about 0.6 to about 0.9 of the vancomycin solubility limit corresponds to >6% to about >9% w/v vancomycin, which is much higher than the vancomycin concentration range (0.1% and about 5% w/v) useful for the current invention.

None of above related art discloses a stable vancomycin solution composition of this invention, nor teaches a method for using tryptophan to stabilize vancomycin in solution. There still is a need for a new vancomycin solution formulation that is aqueous, ready-to-use, injectable and stable for at least 12 months in a non-frozen form.

SUMMARY OF THE INVENTION

In one aspect, this invention provides a vancomycin solution formulation that is non-frozen, aqueous, stable and ready-to-use.

The present invention provides compositions of stable, ready-to-use, aqueous vancomycin solutions comprising, consisting essentially of, or consisting of, vancomycin, tryptophan and water.

The present invention provides methods to stabilize vancomycin in water by inhibiting physical and chemical degradation of vancomycin by including tryptophan in the same solution.

The present invention provides methods to stabilize vancomycin in water by preventing formation of CDP-1s by including tryptophan in the same solution.

The present invention provides methods to stabilize vancomycin in water by preventing, or retarding precipitation of the CDP-1s by including tryptophan in the same solution.

The present invention provides stable aqueous solutions of vancomycin comprising vancomycin at any concentration up to its solubility limit, which is about 12% w/v, and tryptophan at any concentration up to its solubility limit, which is about 2.5% w/v. Note that tryptophan solubility in water is increased from about 1.4% w/v without vancomycin in the same solution to about 2.5% w/v in presence of vancomycin in the same solution. The utility of these solutions is that they keep vancomycin stable and permit vancomycin to be stored as a ready-to-use liquid that does not require either freezing or converting vancomycin into dry powder in order to maintain its stability.

The present invention also provides a method of inhibiting vancomycin degradation in water using vancomycin at any concentration up to near its solubility limit, which is about 12% w/v (120 mg/mL), and tryptophan at any concentration up to its solubility limit, which is about 2.5% w/v (25 mg/mL).

The vancomycin solutions of this invention of particular interest comprise vancomycin at any concentration between about 0.1% w/v and about 12% w/v and tryptophan at a concentration between about 0.1% w/v and about 2.5% w/v. Preferred solutions comprise vancomycin at about 0.5% w/v, about 1% w/v or about 5% w/v and tryptophan at a concentration between about 0.3% and 1.5% w/v.

The vancomycin solutions of this invention comprise vancomycin and tryptophan being or partially being in the form of a non-covalent, reversible and dissociable molecular complex as demonstrated by a phase solubility diagram (Example 1). A preferred molar mixing ratio (vancomycin-to-tryptophan) for such complex formation is between about 10:1 and 1:20, more preferably between 10:1 and 1:5, and most preferably between about 5:1 and 1:1, as measured according to the phase solubility diagram method in Example 1.

The benefits provided by the inclusion of tryptophan in a vancomycin solution are closely related to a novel method of inhibiting degradation of vancomycin by tryptophan. It was surprisingly discovered by this inventor that tryptophan stabilizes vancomycin by inhibiting or preventing its degradation to form various impurities including the CDP-1s. Moreover, this method also inhibits precipitation of vancomycin degradation product(s) and allows the solution compositions of this invention to pass the particulate matter test according to the United State Pharmacopeia (USP) specifications for parenteral drugs.

Preferred methods of the current invention comprise combining between about 0.1% and about 12% w/v vancomycin and between about 0.1% and 2.5% w/v tryptophan in an aqueous solution.

The present invention also provides methods of combining vancomycin and tryptophan to form a solution in water comprising (1) adding and dissolving tryptophan in water first and then adding and dissolving vancomycin in the same solution, (2) adding and dissolving tryptophan and vancomycin in the same solution, and (3) adding and dissolving vancomycin in water first and then adding and dissolving tryptophan in the same solution.

The present invention further provides methods to treat or prevent diseases in a human or animal patient by administering a composition to the patient comprising vancomycin, tryptophan and water. The preferred routes of administration comprise injection, instillation, topical, ophthalmic, otic, intranasal, or intravaginal application.

In another aspect, this invention provides a vancomycin solution formulation that is suitable for injection or for topical, inhalation, instillation, ophthalmic, otic, intranasal, intravaginal or rectal applications.

In yet another aspect, this invention provides a solution formulation comprising, consisting essentially of, or consisting of vancomycin, tryptophan and water.

In yet another aspect, this invention provides a solution formulation comprising a molecular complex formed by vancomycin and tryptophan.

This invention also provides a method to stabilize vancomycin in solution by adding tryptophan to the same solution to inhibit vancomycin degradation to form various impurities including CDP-1s.

This invention also provides a method to stabilize vancomycin in solution by adding tryptophan to the same solution to inhibit precipitation of vancomycin degradation product(s) including CDP-1s.

This invention also provides a method to make a stable vancomycin solution formulation comprising vancomycin, tryptophan and water.

In yet another aspect, this invention provides a method for treatment or prophylaxis for a patient by administering a vancomycin formulation comprising vancomycin, tryptophan and water.

These and other aspects, which will become apparent during the following description, have been achieved by the inventor's discovery that tryptophan at certain concentrations can be useful for stabilizing vancomycin in water.

DETAILED DESCRIPTION OF THE INVENTION

I. Definitions

The various terms used herein shall have the following definitions:

As used herein, "about" describes a quantity with a range covering 10% expansion from both sides of the target value. For example, "about 100" means any value between 90 and 110 and including 90 and 110 and the numbers in between.

As used herein, an "acid" refers to any organic or inorganic acid that is suitable for pharmaceutical use. The acids that have previously approved by the FDA for use in injectable or other solution drugs or are listed on the FDA's Inactive Ingredient List are preferred. Acids that are particularly useful for this invention include, but are not limited to, acetic acid, ascorbic acid, aspartic acid, benzenesulfonic, benzoic acid, citric acid, formic acid, fumaric acid, hydrochloric acid, hydrobromic acid, lactic acid, lactobionic acid, maleic acid, malic acid, malonic acid, methanesulfonic acid, phosphoric acid, propionic acid, succinic acid, sulfuric acid, and tartaric acid.

An "antioxidant" is a pharmaceutical additive that can be added to a liquid composition to prevent oxidation of the active drug or an inactive component. Antioxidants include, but are not limited to, reducing agents, metal ion chelating agents and inert gases.

As used herein, "aqueous" means that the composition is made with water as a liquid vehicle and is substantially free of an organic solvent.

As used herein, the phrase "clear" or "precipitate-free" means a solution composition that exhibits no visible precipitates or particles OR that it passes the USP test specification for "PARTICULATE MATTER IN INJECTIONS" as described in USP monograph <788>. Meeting the USP <788> specification is generally required for all injectable solution formulations in order to be considered safe for human use.

Figure 1:
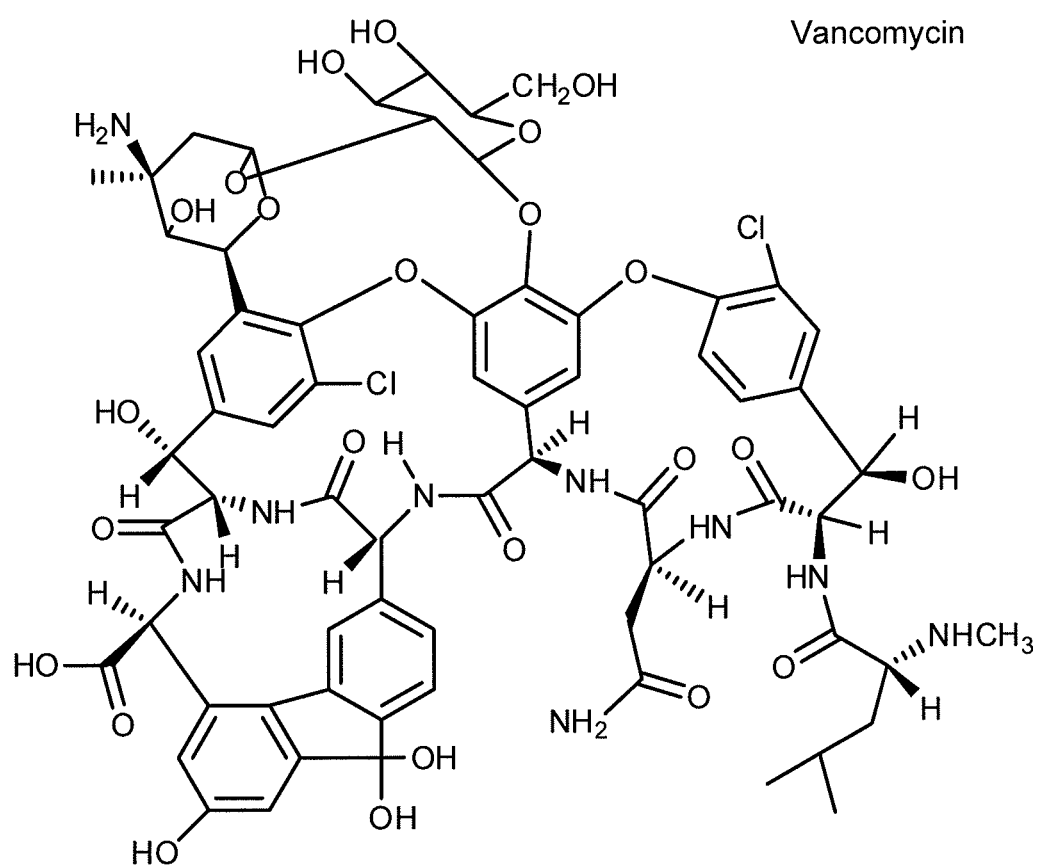
FIG. 1 shows the chemical structure of vancomycin.
Figure 2:
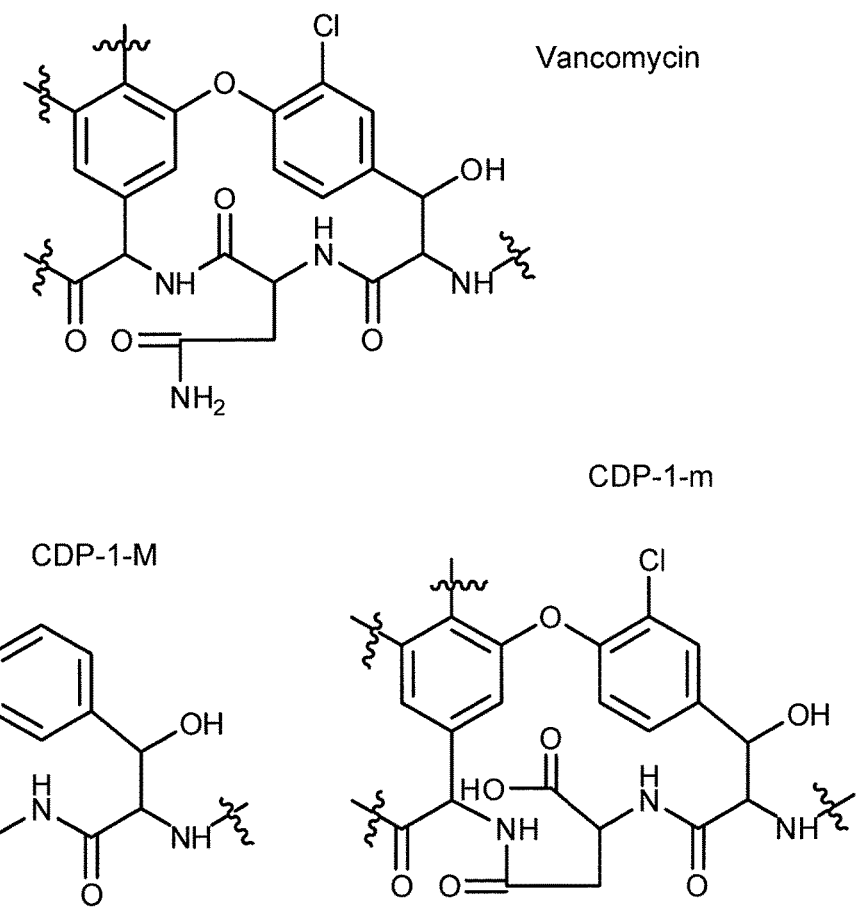
FIG. 2 shows vancomycin and CDP-1 structures.

As used herein, "CDP-1" or "vancomycin CDP-1" refers to products of deamidation of the asparagine residue in vancomycin or CDP-1-m and CDP-1-M as shown in FIG. 2. Vancomycin deamidation results in the formation of an isoaspartate-containing degradant, Crystalline Degradation Product-1 (CDP-1), which exists as two rotamers, CDP-1-m and CDP-1-M (Harris C M, Kopecka H, Harris T M. 1983. Vancomycin: Structure and transformation to CDP-1. J. Am Chem Soc 105:6915-6922). In an aqueous solution, CDP-1s appear to be the most prominent degradation products formed over time. CDP-1s are readily detected by HPLC analysis. As used in the USP, CDP-1-m and CDP-1-M may also be referred to as "Resolution Compound 1" and "Resolution Compound 2", respectively. Due to their lack of solubility in water, CDP-1s readily precipitate in water, rendering the solution unsafe for injection or for other pharmaceutical applications.

As used herein, "FDA" refers to the US Food and Drug Administration.

As used herein, "filterable" means the ability of a liquid to pass through a filter membrane of a certain pore size such as 0.2 microns. The vancomycin solution compositions of the present invention are filterable.

As used herein, an "injectable" refers to a formulation that can be injected safely by intravenous, intra-arterial, subcutaneous, intramuscular, intradermal, intracavernous or other route of injection.

The term "metal ion chelating agent or chelator" includes metal ion chelators that are safe to use in an injectable product. A metal ion chelator functions by binding to a metal ion and thereby reduces the catalytic effect of that metal ion in the oxidation, hydrolysis or other degradation reactions. Metal chelators that are useful in this invention may include ethylenediaminetetraacetic acid (EDTA, edetate), glycine and citric acid and the respective salts or a mixture thereof. Examples of the preferred chelators include sodium, potassium or calcium salts of EDTA. The vancomycin composition of the present invention may optionally contain a chelator.

Figure 3:
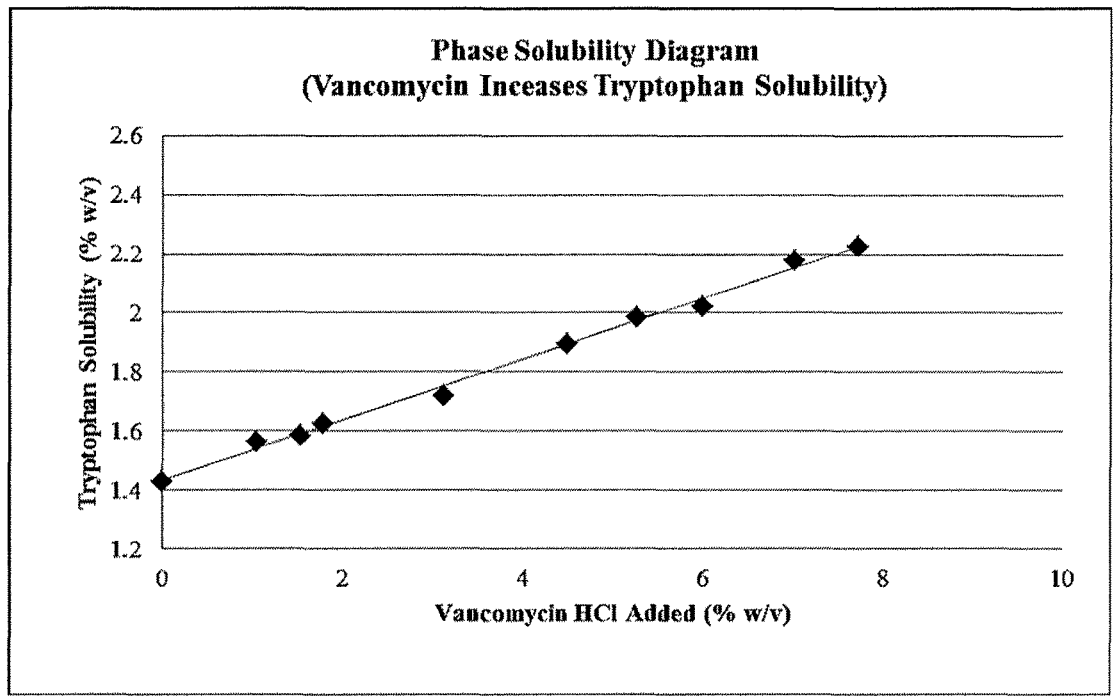
FIG. 3 shows the phase solubility diagram of tryptophan in the presence of vancomycin in the same solution or increases in tryptophan solubility by vancomycin.

As used herein, "molecular complex" means a special interaction between two molecules that are not covalently bonded. The presence of molecular complex is suggested when certain changes in physical or chemical properties (e.g., stability or solubility) of the molecules involved. One of the methods to detect molecular complex formation is the phase solubility diagram which measures changes in solubility of one molecule ("substrate") as a function of the other molecule ("complexing agent") (T. Higuchi and J. L. Lach, J. Am. Pharm. Assoc., Sci. Ed. 43, 349, 525, 527, 1954). To demonstrate the molecular complex formed between vancomycin and tryptophan, solubility of tryptophan in water was measured in presence of vancomycin at various concentrations, to generate a phase solubility diagram (FIG. 3). The data shows that vancomycin increases tryptophan solubility in a linear fashion (FIG. 3), indicating tryptophan is able to form a molecular complex with vancomycin and that the vancomycin-complexed tryptophan has a greater solubility (>0.07M or >1.4% w/v) in water than the uncomplexed tryptophan (about 0.07M or 1.4% w/v). Based on the slope of the phase solubility diagram, the stoichiometric molar ratio of the vancomycin:tryptophan molecular complex formed is estimated at about 1.1:1 to 1.4:1 (vancomycin-to-tryptophan molar ratio) or 7.7:1 to 9.7:1 (vancomycin-to-tryptophan weight ratio) (Example 1). For the same reason, the improved stability of vancomycin by tryptophan disclosed in the compositions of present invention is also thought to be a result of the molecular complex formed between vancomycin and tryptophan (Example 4). In one aspect, the present invention provides such a vancomycin and tryptophan in all such ratios, for example, of about 1.1:1 to 1.4:1 (vancomycin-to-tryptophan molar ratio) or 7.7:1 to 9.7:1 (vancomycin-to-tryptophan weight ratio) as measured by the phase solubility diagram method in Example 1.

Figure 4:
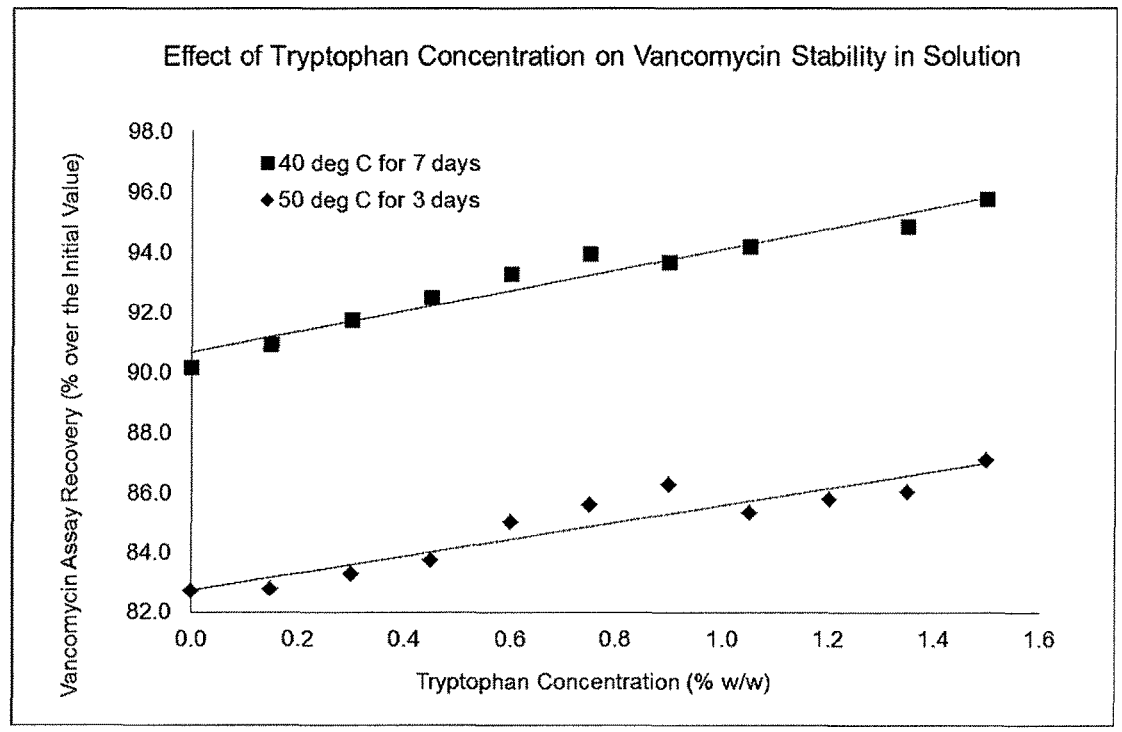
FIG. 4 shows vancomycin stability improves with increase in tryptophan concentration.

For a fixed concentration of vancomycin, the more tryptophan added to the same solution, the better the stability of vancomycin is in solution (FIG. 4). For stabilizing vancomycin in solution, a mixture of vancomycin and tryptophan may also be used in which only a part of tryptophan or vancomycin is in the molecular complex form whereas the remaining exists in the free, uncomplexed form. For example, in a 10:1 molar mixture of vancomycin to tryptophan, only about 10% of the vancomycin may form a complex with tryptophan. Nevertheless, such partial formulation of a molecular complex is still beneficial for stability of vancomycin in solution. The desired molar mixing ratio of vancomycin:tryptophan in the compositions of present invention is between about 10:1 and 1:20. The special interaction responsible for the vancomycin:tryptophan molecular complex may include, but not limited to, hydrogen bond, van der Waals force, π-interactions, hydrophobic effects, and other possible intermolecular interactions. It is important to note that such molecular complexes are non-covalent and completely dissociable with no new chemical entity being formed, and that a tryptophan-stabilized vancomycin does not involve formation of a new salt, a pro-drug or a derivative of vancomycin. In a vancomycin solution of the present invention, both vancomycin and tryptophan remain as two separate, structurally unchanged chemicals, allowing tryptophan to be regarded as a bona fide excipient. Moreover, the inclusion of tryptophan in the same solution with vancomycin does not alter the antimicrobial potency of vancomycin.

As used herein, the term "parenteral" means a route of administration of a drug/preparation by some means other than oral, topical, or rectal intake, particularly intravenously or by injection.

As used herein, "% Impurity" referred to a peak area of a vancomycin-related impurity to the total peak area of all vancomycin-related peaks including the parent peak of vancomycin measured by HPLC at 280 nm detection wavelength and calculated as follows: % Impurity=peak area of that impurity÷total peak area of all vancomycin-related peaks×100.

As used herein, "pH" is a measure of the acidity or basicity of an aqueous solution. The pH determination of a composition of the present invention is typically performed with a pH meter consisting of a glass electrode connected to an electronic meter that measures and displays the pH. The pH meter is calibrated using aqueous standard pH buffers. Solutions with a pH less than 7 are said to be acidic and solutions with a pH greater than 7 are basic or alkaline. Pure water has a pH very close to 7.

As used herein, "preservative" is a pharmaceutical additive that can be added to a liquid composition to inhibit the growth of bacteria and fungi. The antimicrobial preservatives useful in the present invention include, but are not limited to, cresols, phenol, benzyl alcohol, ethanol, chlorobutanol, parabens, imidurea, benzalkonium chloride, EDTA or its salt, or a combination thereof. The vancomycin composition of the present invention may optionally contain a preservative.

As used herein, the term "ready-to-use" means a liquid drug formulation that can be used directly, i.e., injected, diluted or applied without the need for reconstitution.

As used herein, the term "reconstitution" refers to the process of returning a dry powder, or a dehydrated, concentrated or lyophilized state to the liquid state by adding water or other liquid diluent.

As used herein, the term "RLD" or "Reference Listed Drug" refers to "Vancomycin Hydrochloride for Injection, USP", which is currently marketed in the US, manufactured by Hospira Inc. and available in vials (containing 500 mg, 750 mg, 1 g, 5 g and 10 g vancomycin sterile dry powder per vial).

As used herein, the term "solubility" means that a solute has reached its maximum concentration in a solvent. For example, the solubility in water is about 12% w/v or 120 mg/mL for vancomycin and about 14 mg/mL for tryptophan. Due to the molecular complex formation, the solubility of tryptophan is increased in presence of vancomycin allowing for use of tryptophan at a concentration up to about 5% or 50 mg/mL, which exceeds its intrinsic solubility of 14 mg/mL. The vancomycin solutions of this invention comprise between about 0.1% and about 12% w/v vancomycin and between about 0.1% w/v and about 5% w/v tryptophan, preferably between about 0.1% w/v and about 2.5% w/v tryptophan.

As used herein, "solution" refers to a clear, homogeneous liquid mixture composed of only one phase.

As used herein, the term "substantially free" means less than 1% of the total composition weight. For example, the vancomycin solutions of this invention are substantially free of alcohol.

As used herein, "stable" means the composition retains no less than 90% of the initial vancomycin concentration (or assay) after 18 months at a refrigerator temperature (2-8° C.).

As used herein, the term "tonicity adjuster" means certain excipients that are added to liquid formulation to increase its osmotic pressure. For an injectable composition, it is desired to adjust its osmotic pressure to be equivalent to the normal saline ("isosmotic or isotonic"). The tonicity adjusters useful for the composition of the present invention may include, but are not limited to injectable salts, polyols, sugars or amino acids. Exemplary salts sodium chloride, sodium acetate, sodium phosphate, potassium chloride, exemplary polyols are glycerol, mannitol, sorbitol, exemplary sugars are dextrose, lactose, trehalose, and sucrose, and exemplary amino acids are glycine, alanine, lysine, proline, histidine and tryptophan.

As used herein, "tryptophan" refers to the amino acid having the empirical formula: $C_{11}H_{12}N_2O_2$, CAS#: 73-22-3 and a molecular weight of 204.23, other amino acids that contains a tryptophan-like structure in either the L- or D-form or a mixture thereof, such as N-acetyl-tryptophan, serotonin, melatonin, a short peptide containing tryptophan or a salt thereof. The preferred tryptophan is L-tryptophan.

As used herein, "USP" means the current edition of the United States Pharmacopeia.

As used herein, "vancomycin" refers to the glycopeptide having the empirical formula: $C_{66}H_{75}Cl_2N_9O_{24}$, CAS#: 1404-90-6 and a molecular weight of 1,449.3 or another glycopeptide that contains a vancomycin-like structure such as norvancomycin, teicoplanin, telavancin, bleomycin, ramoplanin, and decaplanin, or a salt thereof. The preferred vancomycin salt is vancomycin hydrochloride salt, vancomycin HCl or vancomycin chloride.

As used herein, the term "%" means the weight by volume percentage, or % w/v. For example, 1% w/v means one gram in 100 mL or 10 mg/mL.

II. Description

In an aspect, the present invention provides a solution formulation, comprising:
   a. vancomycin at a concentration between about 0.1% w/v to about 12% w/v
   b. tryptophan at a concentration between about 0.1% w/v and about 2.5% w/v, and
   c. water.

In one aspect, the solution composition of this invention remains clear or precipitate-free for 18 months at 2-8° C. or for 1 month at 25° C.

In one aspect, the composition of this invention contains 0.1% w/v to 12% w/v vancomycin (corresponding to 1 mg/mL to 120 mg/mL, or 0.0007 M to 0.084 M vancomycin). In a more preferred aspect, the composition of this invention contains about 0.5% w/v, 1% w/v or 5% w/v vancomycin. In yet another preferred aspect, the composition of this invention contains 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.5, 4, 5, 6, 7, 8, 9, 10, 11 and 12% w/v vancomycin.

In one aspect, the composition of this invention contains 0.1% w/v to 5% w/v tryptophan (corresponding to 1 mg/mL to 50 mg/mL, or 0.0049 M to 0.246 M tryptophan). In a preferred aspect, the composition of this invention contains 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, or 2.5% w/v tryptophan.

In one aspect, the composition of this invention contains a vancomycin:tryptophan mixture or complex where the ratio of vancomycin-to-tryptophan is between about 100:1 and 1:25 about by weight and preferably between about 10:1 and 1:20 by weight.

In another aspect, the composition of this invention has pH between about 3 and about 6. In a preferred aspect, the composition of this invention has pH of 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5, 5.2, 5.5, or 6.0.

In another aspect, the composition of this invention has pH between about 3 and about 6 which is adjusted using an acid. The preferred acid is hydrochloric acid.

In yet another aspect, the composition of this invention comprises a preservative. The preferred preservative is benzalkonium chloride, cresol, metacresol (m-cresol), phenol, parabens, benzyl alcohol, EDTA or a mixture thereof. The concentrations may be used are about 0.01% to 1% for benzalkonium chloride, 0.08 to 0.315% for cresol/metacresol, 0.06 to 1.3% for phenol, 0.01 to 1.5% for a paraben, 0.05 to 10% for benzyl alcohol, 0.005 to 0.2% for EDTA disodium, and 0.005 to 0.34% for EDTA calcium disodium.

In one aspect, the composition of this invention further contains an antioxidant. The useful antioxidants may include, but not limited to, an inert gas, methionine, cysteine, dextrose, fructose, lactose, and a salt of edetate (EDTA), or combination thereof. A preferred antioxidant is a combination of methionine and EDTA. The concentration of each antioxidant may be determined based on its stabilizing effect on vancomycin in the composition of this invention and its safety to the patient. A normal range of concentration for each antioxidant can be found in the FDA's Inactive Ingredient List. For example, the methionine concentration range useful for injectable formulations is 0.01% to 49.2%.

In an aspect, the present invention provides a clear, stable and ready-to-use solution formulation, comprising:
a. about 0.1% w/v to about 12% w/v vancomycin;
b. about 0.1% w/v to about 2.5% w/v tryptophan; and
c. water, wherein the pH of the solution is between about 3 and about 6.

In an aspect, the present invention provides a clear, isotonic and ready-to-use solution formulation, comprising:
a. about 0.5% w/v vancomycin;
b. about 0.5% w/v tryptophan;
c. sodium chloride added to the isotonic concentration; and
d. water, wherein the pH of the solution is between about 3 and about 6.

In an aspect, the present invention provides a clear, isotonic and ready-to-use solution formulation, comprising:
a. about 1% w/v vancomycin;
b. about 1.0 to 1.4% w/v tryptophan;
c. sodium chloride added to the isotonic concentration; and
d. water.

In an aspect, the present invention provides a clear and ready-to-use solution formulation, comprising:
a. about 5% w/v vancomycin;
b. about 1.5% w/v tryptophan; and
c. water.

In another aspect, the present invention provides a method to prepare a solution formulation, comprising: (1) dissolving vancomycin in water first and then dissolving tryptophan in the same solution to form a clear solution containing about 0.1% w/v to about 12% w/v vancomycin and 0.1% w/v to about 2.5% w/v tryptophan, and (2) adjusting the pH to between about 3 and about 6 using an acid.

In another aspect, the present invention provides a method to prepare a solution formulation, comprising: (1) dissolving tryptophan in water first then dissolving vancomycin in the same solution to form a clear solution containing about 0.1% w/v to about 12% w/v vancomycin and 0.1% w/v to about 2.5% w/v tryptophan, and (2) adjusting the pH to between about 3 and about 6 using an acid.

In another aspect, the present invention provides a method to prepare a solution formulation, comprising: (1) dissolving tryptophan and vancomycin together in the same solution to form a clear solution containing about 0.1% w/v to about 12% w/v vancomycin and 0.1% w/v to about 2.5% w/v tryptophan, and (2) adjusting the pH to between about 3 and about 6 using an acid.

In another aspect, the present invention provides a method to prepare a solution formulation, comprising: (1) combining vancomycin and tryptophan, (2) dissolving them together in water to form a clear solution containing about 0.1% w/v to about 12% w/v vancomycin and 0.1% w/v to about 2.5% w/v tryptophan, and (3) adjusting the pH to between about 3 and about 6 using an acid.

In another aspect, the present invention provides a method to prepare a solution formulation, comprising the addition of water to a solid composition comprising vancomycin, tryptophan and optionally an acid. The said solid composition contains the calculated amounts of vancomycin, tryptophan and acid such that upon reconstitution with water, it forms a clear solution containing about 0.1% w/v to about 12% w/v vancomycin and 0.1% w/v to about 2.5% w/v tryptophan and having a pH at between about 3 and about 6.

The solution formulation of the present invention can be administered as is (undiluted) or diluted prior to administration. Dilutions can be made using a 5% or 10% dextrose solution or another injectable diluent or infusion fluid. The route of administration may include, but is not limited to, injection, instillation, inhalation, oral, otic, nasal, topical, ophthalmic, vaginal, and rectal administration. The solution formulation of the present invention can be delivered using needles/syringes, infusion sets, catheters, applicators, bottles, sprayers, inhalation devices, or as/from a wound dressing.

In one aspect, the solution formulation of the present invention is compatible with the same infusion fluids that are permitted for the RLD, including: 5% Dextrose Injection, USP, 5% Dextrose and 0.9% Sodium Chloride Injection, USP Lactated Ringer's Injection, USP 5% Dextrose and Lactated Ringer's Injection, Normosol-M and 5% Dextrose, 0.9% Sodium Chloride Injection USP, ISOLYTE E and combinations thereof.

In one aspect, a vancomycin solution formulation of the present invention exhibits the same antibacterial activity as a vancomycin solution in water at the same vancomycin concentration without tryptophan.

In one aspect, the solution composition of this invention wherein vancomycin is stable for 18 months at 2-8° C. or for 1 month at 25° C.

In one aspect, the solution composition of this invention remains clear or precipitate-free for 18 months at 2-8° C. or for 1 month at 25° C.

In one aspect, the % Impurity of any individual vancomycin-related impurity in the solution composition of this invention is no more 4% for 12 months at 2-8° C. or for 1 month at 25° C.

In one aspect, the composition of this invention is capable of passing the USP test specification for "PARTICULATE MATTER IN INJECTIONS" as described in the USP monograph <788> after storage at 2-8° C. for 18 months or for 1 month at 25° C.

In one aspect, the composition of this invention is capable of passing the USP test assay and impurity specifications as defined in the "Vancomycin for Injection, USP" monograph (USP-NF 28).

In one aspect, composition of this invention has an osmotic pressure of about 200 to 600 mOsmol/L.

In one aspect, composition of this invention containing about 5 to 10 mg/mL vancomycin and is isotonic.

In one aspect, tryptophan in the solution composition of this invention remains stable without any tryptophan-related impurity formed to a concentration greater than 0.1% for 6 months at 2-8° C.

In one aspect, the composition of this invention is ready-to-use.

In one aspect, the composition of this invention is filterable through a 0.2 or 0.45-micron membrane.

In one aspect, the composition of this invention is filled in glass vials, syringes, dropper bottles, tubes, applicators, unit dispensers, infusion bags, sprayers, inhalation devices or other pharmaceutical containers.

In one aspect, the composition of this invention is filled in glass vials, syringes, dropper bottles, tubes, applicators, unit dispensers, infusion bags, sprayers, inhalation devices or other pharmaceutical containers with inert gas such as nitrogen gas filled in the headspace.

In one aspect, the composition of this invention is used for the treatment or prevention of bacterial infection including staphylococcal infections.

In one aspect, the composition of this invention is used for treatment or prevention of infections caused by methicillin-resistant strains of *staphylococcus* (MRSA).

In one aspect, the composition of this invention containing about 5 to 10 mg/mL vancomycin is injected directly without any further dilution or mixing.

In one aspect, the composition of this invention containing about 50 mg/mL or more vancomycin is diluted in one of the compatible infusion fluids first to about 5 to 10 mg/mL and then injected.

The present invention will be further understood by reference to the following non-limiting examples.

EXAMPLE 1

The aim of this study was to demonstrate molecular complex formulation between vancomycin and tryptophan using a phase solubility diagram based on measuring tryptophan solubility in solutions of increasing vancomycin concentration. In addition, this study intended to determine the stoichiometric ratio of such molecular complex formed. To obtain a phase solubility diagram of tryptophan, pre-calculated amounts of tryptophan, vancomycin and water were added into a plastic tube to form a suspension in which vancomycin was completed dissolved but tryptophan was not completed dissolved, the suspension was adjusted to pH 6.2, mixed at room temperature (RT) overnight to reach dissolution/re-crystallization equilibrium, and then filtered through a 0.2-micorn filter membrane. The filtrate was diluted and analyzed by HPLC (using the USP HPLC vancomycin assay method) to determine the concentrations of tryptophan and vancomycin. The solubility of tryptophan measured and the concentration of vancomycin added measured in each suspension sample are provided in the Table below:

| Sample ID | pH | Tryptophan Solubility Determined | | | Vancomycin Added | | | Tryptophan Solubility Increase | | Molecular Complex Stoichiometric Ratio (Vancomycin:Tryptophan) | |
|---|---|---|---|---|---|---|---|---|---|---|---|
| | | mg/mL | % w/v | M | mg/mL | % w/v | M | mg/mL | M | Weight Ratio | Molar Ratio |
| 1 | 6.25 | 14.30 | 1.43 | 0.070 | 0.00 | 0.00 | 0.000 | 0 | 0.000 | No complex | No complex |
| 2 | 6.28 | 15.65 | 1.565 | 0.077 | 10.38 | 1.04 | 0.007 | 1.35 | 0.007 | 7.7:1 | 1.1:1 |
| 3 | 6.20 | 16.27 | 1.627 | 0.080 | 17.76 | 1.78 | 0.012 | 1.97 | 0.010 | 9.0:1 | 1.3:1 |
| 4 | 6.13 | 15.86 | 1.586 | 0.078 | 15.28 | 1.53 | 0.011 | 1.56 | 0.008 | 9.8:1 | 1.4:1 |
| 5 | 6.21 | 17.18 | 1.718 | 0.084 | 31.08 | 3.11 | 0.021 | 2.88 | 0.014 | 10.8:1 | 1.5:1 |
| 6 | 6.26 | 18.95 | 1.895 | 0.093 | 44.90 | 4.49 | 0.031 | 4.65 | 0.023 | 9.7:1 | 1.4:1 |
| 7 | 6.20 | 19.86 | 1.986 | 0.097 | 52.83 | 5.28 | 0.036 | 5.56 | 0.027 | 9.5:1 | 1.3:1 |
| 8 | 6.22 | 20.23 | 2.023 | 0.099 | 60.02 | 6.00 | 0.041 | 5.93 | 0.029 | 10.1:1 | 1.4:1 |
| 9 | 6.23 | 21.78 | 2.178 | 0.107 | 70.12 | 7.01 | 0.048 | 7.48 | 0.037 | 9.4:1 | 1.3:1 |
| 10 | 6.20 | 22.29 | 2.229 | 0.109 | 77.20 | 7.72 | 0.053 | 7.99 | 0.039 | 9.7:1 | 1.4:1 |

FIG. 3 shows the phase solubility diagram of tryptophan or increase in tryptophan solubility by vancomycin.

From the tryptophan phase solubility diagram, it is clear that a non-covalent molecular complex(es) is formed between vancomycin and tryptophan. The stoichiometric ratio of vancomycin-to-tryptophan in such complex may vary from about 1:1 to 1.4:1 (molar ratio) or 7.7:1 to 9.7:1 (weight ratio), meaning that each tryptophan molecule can form a molecular complex with about one or more molecules of vancomycin. The molecular complex formation increased the apparent solubility of tryptophan because tryptophan in the vancomycin-tryptophan complex form is more soluble than tryptophan without vancomycin present in the same solution. In other words, through the addition of vancomycin, the solubility of tryptophan was increased from 1.43% (with 0% vancomycin added), to 2.2% (with 7.7% vancomycin added), to an estimated 2.5% (with 10% vancomycin added). For the same reason, the vancomycin-tryptophan molecular complex formation increased the stability of vancomycin in the solution compositions of the current invention because vancomycin in the complex is more stable than vancomycin alone (Example 4).

EXAMPLE 2

The aim of this study was to compare effects of various ingredients on vancomycin stability in a solution in order to identify a stabilizer that can slow the degradation of vancomycin in solution. Each solution sample (coded with an F-#) was prepared by dissolving vancomycin HCl to 1% concentration, along with stabilizer added at the concentrations listed in the Table below. Each solution was adjusted to about pH 4.7 and stored at 2-8° C. and 50° C. for 2 days.

The stability of vancomycin was indicated by vancomycin recovery (% over the initial concentration) after storage at a selected temperature. The concentration of vancomycin or vancomycin assay was measured using HPLC method (USP Vancomycin Assay method). The relative stability of vancomycin in each solution was expressed in vancomycin concentration or assay recovery (% over the initial concentration). The test sample compositions and test results are shown in the Table below.

| % wt | F-18 | F-29 | F-30 | F-31 | F-32 | F-33 | F-34 | F-35 | F-36 | F-37 | F-38 | F-39 | F-40 | F-41 | F-42 |
|---|---|---|---|---|---|---|---|---|---|---|---|---|---|---|---|
| Composition | | | | | | | | | | | | | | | |
| Vancomycin HCl | 1 | 1 | 1 | 1 | 1 | 1 | 1 | 1 | 1 | 1 | 1 | 1 | 1 | 1 | 1 |
| NaCl | 0.8 | 0.8 | 0.8 | 0.8 | 0.8 | 0.8 | 0.8 | 0.8 | 0.8 | 0.8 | 0.8 | 0.8 | 0.8 | 0.8 | 0.8 |
| Zinc chloride | | 0.09 | | | | | | | | | | | | | |
| Magnesium chloride | | | 0.64 | | | | | | | | | | | | |
| Ferric chloride | | | | 1.09 | | | | | | | | | | | |
| Calcium chloride | | | | | 0.75 | | | | | | | | | | |
| Tryptophan | | | | | | 1.37 | | | | | | | | | |
| N-acetyl-tryptophan | | | | | | | 1.65 | | | | | | | | |
| Phenylalanine | | | | | | | | 1.11 | | | | | | | |
| Tyrosine | | | | | | | | | 1.22 | | | | | | |
| Aspartic acid | | | | | | | | | | 0.90 | | | | | |
| Glycylglycine | | | | | | | | | | | 0.89 | | | | |
| Histidine | | | | | | | | | | | | 1.04 | | | |
| Lysine | | | | | | | | | | | | | 0.98 | | |
| Alanine | | | | | | | | | | | | | | 0.60 | |
| DMPG Na* | | | | | | | | | | | | | | | 4.26 |
| Solution pH | 4.67 | 4.74 | 4.76 | 4.61 | 4.8 | 4.74 | 4.7 | 4.72 | 4.64 | 4.76 | 4.75 | 4.62 | 4.63 | 4.8 | 4.66 |
| Test results | | | | | | | | | | | | | | | |
| Vancomycin Assay Recovery (%) at 50° C. for 2 days | 87.8 | 87.7 | 88.6 | 85.3 | 89.4 | 90.9 | 90.1 | 88.9 | 88.8 | 86.8 | 84.3 | 73.6 | 86.9 | 82.7 | 86.7 |
| Vancomycin Assay Recovery (%) at 50° C. for 4 days | 78 | 78 | 76.9 | 72.4 | 79.2 | 85.3 | 81 | 79.3 | 76.1 | 75.1 | 71.5 | 51.8 | 80.4 | 70.7 | 72.7 |

*1,2-dimyristoyl-sn-glycero-3-phosphoglycerol, sodium salt

The results from this study indicate that tryptophan or a tryptophan analog (N-acetyl-tryptophan) is capable of slowing down the degradation of vancomycin in solution. Other additives showed no or a negative effect on vancomycin stability in solution.

EXAMPLE 3

The aim of this study was to compare various amino acids, including tryptophan, on their effects on vancomycin stability in an aqueous solution. The solution samples were prepared and tested similarly to Example 2. The sample compositions and test results are shown in the Table below:

| % wt | F-18 | F-43 | F-44 | F-45 | F-46 | F-47 | F-48 | F-49 |
|---|---|---|---|---|---|---|---|---|
| Composition | | | | | | | | |
| Vancomycin HCl | 1 | 1 | 1 | 1 | 1 | 1 | 1 | 1 |
| NaCl | 0.8 | 0.8 | 0.8 | 0.8 | 0.8 | 0.8 | 0.8 | 0.8 |
| Methionine | | 1.00 | | | | | | |
| Alanine | | | 0.60 | | | | | |
| Tryptophan | | | | 1.37 | | | | |
| Cysteine | | | | | 0.82 | | | |
| Arginine | | | | | | 1.17 | | |
| Proline | | | | | | | 0.77 | |
| Asparagine | | | | | | | | 0.89 |
| Solution pH | 4.68 | 4.74 | 4.77 | 4.76 | 4.7 | 4.64 | 4.71 | 4.64 |
| Test results | | | | | | | | |
| Vancomycin Assay Recovery (%) at 50° C. for 2 days | 91.3 | 91.3 | 91.6 | 93.0 | 81.3 | 91.2 | 91.1 | 90.2 |

This study confirmed that tryptophan is capable of slowing down the degradation of vancomycin whereas other amino acids had no or negative effect on vancomycin stability in solution.

EXAMPLE 4

The aim of this study was to demonstrate effect of tryptophan concentration on vancomycin stability in solution. The solution samples were prepared and tested in a similar way as in Example 2. The test sample compositions and test results are shown in the Table below and the effects of tryptophan concentration on vancomycin stability are depicted graphically in FIG. 4.

| % wt | F-50 | F-51 | F-52 | F-53 | F-54 | F-55 | F-56 | F-57 | F-58 | F-59 | F-18 |
|---|---|---|---|---|---|---|---|---|---|---|---|
| Composition | | | | | | | | | | | |
| Vancomycin HCl | 1 | 1 | 1 | 1 | 1 | 1 | 1 | 1 | 1 | 1 | 1 |
| Tryptophan | 1.5 | 1.35 | 1.2 | 1.05 | 0.9 | 0.75 | 0.6 | 0.45 | 0.3 | 0.15 | 0 |
| NaCl | 0.8 | 0.8 | 0.8 | 0.8 | 0.8 | 0.8 | 0.8 | 0.8 | 0.8 | 0.8 | 0.8 |
| pH | 4.87 | 4.81 | 4.82 | 4.86 | 4.86 | 4.87 | 4.84 | 4.81 | 4.9 | 5.12 | 5.25 |
| Test results | | | | | | | | | | | |
| Vancomycin Assay Recovery (%) at 30° C. for 3 days | 100.14 | 98.38 | 97.72 | 98.21 | 97.51 | 98.64 | 98.76 | 98.42 | 97.48 | 96.48 | 97.27 |
| Vancomycin Assay Recovery (%) at 40° C. for 3 days | 95.45 | 94.59 | 95.13 | 94.76 | 94.54 | 94.39 | 94.39 | 94.02 | 92.42 | 93.35 | 91.92 |
| Vancomycin Assay Recovery (%) at 50° C. for 3 days | 87.09 | 86.02 | 85.79 | 85.33 | 86.27 | 85.61 | 85.02 | 83.76 | 83.29 | 82.79 | 82.73 |
| Vancomycin Assay Recovery (%) at 40° C. for 7 days | 95.77 | 94.85 | 84.28 | 94.18 | 93.68 | 93.96 | 93.29 | 92.48 | 91.72 | 90.92 | 90.16 |

FIG. 4 shows vancomycin stability improves with increase in tryptophan concentration. These results reveal that tryptophan improves vancomycin stability in a concentration-dependent fashion, with a higher concentration of tryptophan producing greater vancomycin stability in solution within the tested tryptophan concentration range from 0 to 1.5% w/w.

EXAMPLE 5

Figure 5:
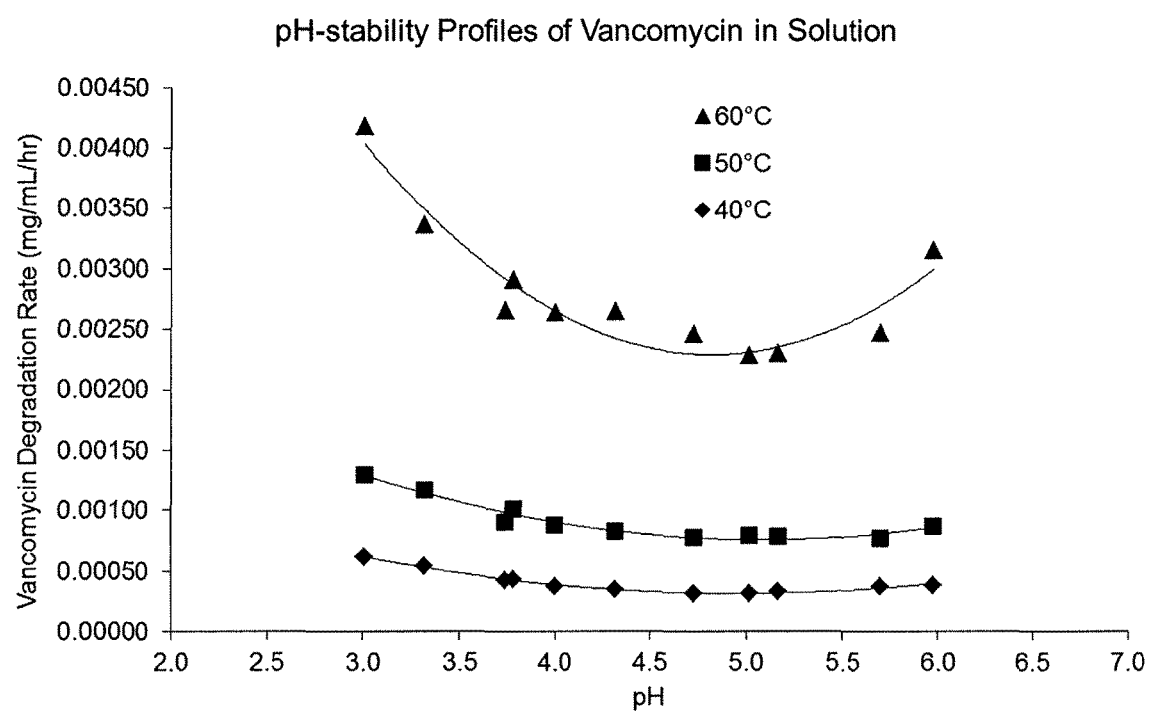
FIG. 5 shows a pH stability profile for vancomycin.

The aim of this study was determine the pH or pH range at which vancomycin is most stable. Each test solution was prepared to contain 5 mg/mL vancomycin HCl and the pH of the solution was adjusted to about 3, 3.3, 3.7, 4, 4.3, 4.7, 5, 5.3, 5.7, or 6 with HCl/NaOH. The solutions were stored at 25, 40, 50 and 60° C. and analyzed for vancomycin concentration after various times by the vancomycin HPLC method. The rate of degradation of vancomycin (mg/mL/hr) was calculated, plotted against the pH of the solution and used to determine the pH or pH range at which vancomycin is most stable. The test results are depicted graphically in FIG. 5. These results reveal that vancomycin is more stable within between pH 3 and 6, preferably between 3.5 and 5.5 and more preferably between 4 and 5.5.

EXAMPLE 6

Multiple batches of the solution formulations of the present invention have been prepared using the following procedure:
Step #1: Weigh out and add L-tryptophan and sodium chloride (as needed) into a clean plastic container.
Step #2: Add Water for Injection, USP (WFI) to about 95% of the batch weight.
Step #3: Mix using a magnetic stir bar to dissolve the solids. To speed up the dissolution, sonication and heating to no more than 50° C. has been applied. The solution obtained is a clear and nearly colorless liquid.
Step #4: Weigh out and add the vancomycin raw material (or Active Pharmaceutical Ingredient or API) to the same container.
Step #5: Mix using a magnetic stir bar to dissolve the solids. Vancomycin dissolves quickly and this process usually takes about 1 hour to complete. The solution obtained is clear and the color may vary from nearly colorless to yellow depending upon the API used and the final concentration of vancomycin. The pH of this solution is usually around 5.5.
Step #6 While stirring, adjust the solution pH to within the target range using 1N hydrochloric acid solution. If pH is overshot, then add 1N sodium hydroxide to adjust back.
Step #7 Add WFI to the final batch weight.
Step #8: Mix using a magnetic stir bar at room temperature to allow the pH to stabilize.
Step #9: Measure the pH. If pH has changed by more than 0.2 units, re-adjust pH with either 1N HCl or 1N NaOH, then mix for an additional 30 minutes.
Step #10: Pass the solution through a sterile 0.2 μm filter to sterilize. Collect the filtrate in a sterile container.
Step #11 Aseptically fill the filtrate into the final containers such as glass vials or prefillable syringes.

EXAMPLE 7

The following batches of the solution formulations of the present invention have been prepared and tested for stability:

| | Formulation code | | | | |
|---|---|---|---|---|---|
| | F51 | F78 | F82 | F82 | F87 |
| Container | 100 mL glass vial | 20 mL glass vial | 10 mL prefillable syringe | 10 mL glass vial | 100 mL glass vial |
| Vancomycin HCl (mg/mL) | 10.40 | 10.40 | 52.23 | 52.23 | 5.20 |
| L-tryptophan (mg/mL) | 13.7 | 10.4 | 15.2 | 15.2 | 5.2 |
| NaCl (mg/mL) | 8.1 | 3.6 | 0 | 0 | 8.1 |
| Source of vancomycin raw material | Lek Pharma | Xellia Pharma | Xinchang Pharma | Xinchang Pharma | Xellia Pharma |

The following stability tests were performed on the solution formulations of the present invention. Whenever applicable, the USP analytical test methods and specifications for "Vancomycin Hydrochloride for Injection, USP" were used.

| Test | Method | Specifications |
|---|---|---|
| Appearance | Visual evaluation | Report clarity, color and presence of solid, e.g., precipitates |
| pH | pH meter | 4-5 |
| Vancomycin assay (mg/mL) | USP HPLC method for "Assay" | NLT 90.0% & NMT 115.0% (USP) |
| Chromatographic Purity (peak area) CDP-1-m (or Resolution Compound 1 per USP) CDP-1-M (or Resolution Compound 2 per USP) Largest Individual Impurity | USP HPLC method for "Chromatographic Purity" | NLT 88.0% of vancomycin B is found & NMT 4.0% of any peak other than the main peak is found (USP) |
| Particulate Matter | The USP<788> method using HIAC | USP spec for Small-Volume Injections, i.e. 10 μm: NMT 6000/container & 25 μm: NMT 600/container |

Formulation Code: F-51 in glass vials
Storage: 2-8° C.
Vial orientation: Upright

| Test | Initial | 19 M | 20 M | 21 M | 22 M | 25 M |
|---|---|---|---|---|---|---|
| Appearance | Amber solution* | No change | No change | No change | No change | Precipitate (Fail) |
| pH | 4.87 | 4.81 | 4.74 | 4.78 | 5.0 | 4.74 |
| Vancomycin Assay or Concentration (mg/mL) | 10.5 | 10.3 | 9.9 | 10.0 | 9.9 | 9.9 |
| Assay Recovery (% over Initial) | 100.0 | 98.0 | 94.1 | 94.8 | 94.1 | 94.0 |
| Vancomycin Purity (% peak area) | 95.5 | 88.9 | 91.4 | 91.5 | 93.2 | 93.7 |
| CDP-1-m (% peak area) | 0.8 | 1.0 | 1.1 | 1.1 | 1.1 | 1.1 |
| CDP-1-M (% peak area) | 0.8 | 5.0** | 2.9 | 2.9 | 1.9 | 1.8 |
| Largest Individual Impurity (% peak area) | 0.8 | 5.0** | 2.9 | 2.9 | 1.9 | 1.8 |
| Particulate Matter | Pass | Pass | Not tested | Not tested | Not tested | Fail |

*The solution prepared with the LEK API is amber whereas solutions prepared with the Xellia or Xinchang API are almost colorless to a faint yellow.
**This high value was determined to be an outlier due to analytical artifact. It is not supported by the HIAC reading or the subsequent monthly HPLC test results.

Three additional solution compositions of vancomycin were prepared according to table below. The solutions were filled into glass vials or pre-sterilized syringes and kept at 2-8° C. and 25° C.

| % w/v | F-87 | F-78 | F-82 |
|---|---|---|---|
| Vancomycin | 0.5 | 1.0 | 5.0 |
| NaCl | 0.8 | 0.356 | 0.0 |
| L-tryptophan | 0.51 | 1.028 | 1.5 |
| Water | QS | QS | QS |
| pH | 4.7 +/− 0.1 | 4.0 +/− 0.1 | 4.0 +/− 0.1 |

The long-term stability of F-87 in glass vials was tested and the test results are provided in the tables below:

Formulation Code: F-78 in glass vials
Storage: 2-8° C.
Vial orientation: upright

| Test | Initial | 1 M | 2 M | 3 M | 6 M | 12 M |
|---|---|---|---|---|---|---|
| Appearance | Clear, nearly colorless solution | No change | No change | Slightly more yellow | Slightly more yellow | Slightly more yellow |
| pH | 4.2 | 4.1 | 4.4 | 4.2 | 4.2 | 4.4 |
| Vancomycin Assay or Concentration (mg/mL) | 10.2 | 10.1 | 10.0 | 9.8 | 10.0 | 9.6 |
| Assay Recovery (% over Initial) | 100.0 | 99.1 | 98.3 | 97.1 | 97.8 | 94.4 |

-continued

| Test | Initial | 1 M | 2 M | 3 M | 6 M | 12 M |
|---|---|---|---|---|---|---|
| Vancomycin Purity (% peak area) | 95.9 | 92.6 | 92.4 | 93.0 | 92.2 | 89.1 |
| CDP-1-m (% peak area) | 0.4 | 0.8 | 1.1 | 1.3 | 1.5 | 1.5 |
| CDP-1-M (% peak area) | 0.04 | 0.1 | 0.3 | 0.7 | 1.7 | 2.9 |
| Largest Individual Impurity (% peak area) | 0.6 | 1.8 | 1.8 | 1.3 | 1.7 | 2.9 |
| Particulate Matter | Pass | Pass | Pass | Pass | Pass | Pass |

Formulation Code: F-78 in glass vials
Storage: 25° C.
Vial orientation: upright

| Test | Initial | 1 M | 2 M |
|---|---|---|---|
| Appearance | Clear, nearly colorless solution | More yellow | Precipitates (Fail) |
| pH | 4.2 | 4.1 | 4.6 |
| Vancomycin Assay or Concnetration (mg/mL) | 10.2 | 9.3 | 8.7 |
| Assay Recovery (% over Initial) | 100.0 | 91.2 | 85.0 (Fail) |
| Vancomycin Purity (% peak area) | 95.9 | 86.7 | 81.4 (Fail) |
| CDP-1-m (% peak area) | 0.4 | 2.4 | 2.4 |
| CDP-1-M (% peak area) | 0.04 | 3.5 | 6.3 (Fail) |
| Largest Individual Impurity (% peak area) | 0.6 | 3.5 | 6.3 (Fail) |
| Particulate Matter | Pass | Pass | Fail |

Formulation Code: F-82 in prefilled syringes
Storage: 2-8° C.
Prefilled syringe orientation: upright

| Test | Initial | 1 M | 2 M | 3 M | 6 M |
|---|---|---|---|---|---|
| Appearance | Clear, slightly yellow solution | No change | No change | No change | No change |
| pH | 4.1 | 4.1 | 4.1 | 4.2 | 4.1 |
| Vancomycin Assay or Concentration (mg/mL) | 50.0 | 51.2 | 51.3 | 47.7 | 51.1 |
| Assay Recovery (% over Initial) | 100 | 102.4 | 102.8 | 96.0 | 102.3 |
| Vancomycin Purity (% peak area) | 95.5 | 94.3 | 95.2 | 93.2 | 93.3 |
| CDP-1-m (% peak area) | 0.6 | 1.2 | 0.8 | 1.0 | 1.1 |
| CDP-1-M (% peak area) | 0.1 | 0.1 | 0.2 | 0.4 | 0.8 |
| Largest Individual Impurity (% peak area) | 0.7 | 1.2 | 1.0 | 1.2 | 1.1 |
| Particulate Matter | Pass | Pass | Pass | Pass | Pass |

Formulation Code: F-82 in prefilled syringes
Storage: 25° C.
Prefilled syringe orientation: upright

| Test | Initial | 1 M | 2 M |
|---|---|---|---|
| Appearance | Clear, slightly yellow solution | No change | Precipitates (Fail) |
| pH | 4.1 | 4.4 | 4.4 |
| Vancomycin Assay or Concentration (mg/mL) | 50.0 | 48.9 | 46.1 |
| Assay Recovery (% over Initial) | 100 | 98.0 | 92.2 |
| Vancomycin Purity (% peak area) | 95.5 | 90.0 | 91.1 |
| CDP-1-m (% peak area) | 0.6 | 2.6 | 2.8 |
| CDP-1-M (% peak area) | 0.1 | 2.2 | 1.8 |
| Largest Individual Impurity (% peak area) | 0.7 | 2.6 | 2.8 |
| Particulate Matter | Pass | Pass | Fail |

Formulation Code: F-82 in glass vials
Storage: 2-8° C.
Vial orientation: upright

| Test | Initial | 3 M | 6 M |
|---|---|---|---|
| Appearance | Clear, lightly yellow solution | No change | No change |
| pH | 4.1 | 4.2 | 4.2 |
| Vancomycin Assay or Concentration (mg/mL) | 50.0 | 49.4 | 50.7 |
| Assay Recovery (% over Initial) | 100 | 99.0 | 101.4 |
| Vancomycin Purity (% peak area) | 95.5 | 93.2 | 93.7 |
| CDP-1-m (% peak area) | 0.6 | 1.0 | 1.1 |
| CDP-1-M (% peak area) | 0.1 | 0.4 | 0.5 |
| Largest Individual Impurity (% peak area) | 0.7 | 1.1 | 1.1 |
| Particulate Matter | Pass | Pass | Not tested |

Formulation Code: F-87 in glass vials
Storage: 2-8° C.
Vial orientation: upright

| Test | Initial | 1 M | 2 M | 3 M |
|---|---|---|---|---|
| Appearance | Clear, nearly colorless solution | No change | No change | No change |
| pH | 4.7 | 4.7 | 4.7 | 5.0 |
| Vancomycin Assay (mg/mL) | 5.1 | 5.1 | 5.0 | 5.0 |
| Assay Recovery (% over Initial) | 100 | 100.1 | 97.9 | 98.0 |
| Vancomycin Purity (% peak area) | 93.8 | 93.3 | 92.9 | 92.2 |
| CDP-1-m (% peak area) | 0.7 | 0.9 | 1.2 | 1.5 |
| CDP-1-M (% peak area) | 0.1 | 0.2 | 0.8 | 0.8 |
| Largest Individual Impurity (% peak area) | 1.7 | 1.7 | 1.8 | 1.8 |
| Particulate Matter | Pass | Pass | Pass | Pass |

Formulation Code: F-87 in glass vials
Storage: 25° C.
Vial orientation: upright

| Test | Initial | 1 M | 2 M |
|---|---|---|---|
| Appearance | Clear, nearly colorless solution | No change | No change |
| pH | 4.7 | 4.9 | 4.8 |
| Vancomycin Assay (mg/mL) | 5.1 | 4.8 | 4.4 |
| Assay Recovery (% over Initial) | 100 | 93.9 | 85.3 |
| Vancomycin Purity (% peak area) | 93.8 | 89.6 | 83.3 |
| CDP-1-m (% peak area) | 0.7 | 1.7 | 1.6 |
| CDP-1-M (% peak area) | 0.1 | 2.6 | 7.3 |
| Largest Individual Impurity (% peak area) | 1.7 | 2.6 | 7.3 |
| Particulate Matter | Pass | Pass | Pass |

These results indicate that the vancomycin solution compositions of this invention are stable for 18 months at 2-8° C. or for 1 month at 25° C.

EXAMPLE 8

The purpose of this study was to demonstrate the stability of a concentrated vancomycin solution after being diluted with intravenous infusion fluids. Infusion fluids were selected based on those listed in the package insert of the RLD, Vancomycin HCl for Injection, USP. Dilutions were prepared in sterile 20 mL glass vials per instructions on the RLD's package insert. Dilutions were stored at 2-8° C. for two weeks as instructed in the RLD's package insert.

The composition of the concentrated vancomycin solution is shown in the table below.

| % w/v | F-82 |
|---|---|
| Vancomycin | 5.0 |
| L-tryptophan | 1.5 |
| Water | QS |
| pH | 4.0 +/- 0.1 |

The infusion fluids evaluated in the study are listed in the table below:
5% Dextrose Injection, USP
5% Dextrose and 0.9% Sodium Chloride Injection, USP
Lactated Ringer's Injection, USP
5% Dextrose and Lactated Ringer's Injection
Normosol-M and 5% Dextrose
0.9% Sodium Chloride Injection, USP
ISOLYTE E The stability of F-82 diluted in infusion fluids was tested and test results are provided in the table below:

| | | Infusion fluid used | | | | | | |
|---|---|---|---|---|---|---|---|---|
| Test | USP Specification | 5% Dextrose Injection, USP | 5% Dextrose and 0.9% Sodium Chloride Injection, USP | Lactated Ringer's Injection, USP | 5% Dextrose and Lactated Ringer's | Normosol-M and 5% Dextrose | 0.9% Sodium Chloride Injection, USP | ISOLYTE E |
| Appearance | Report results | pass | pass | pass | Pass | pass | pass | pass |
| pH | Report results | pass | pass | pass | Pass | pass | pass | pass |
| Osmolality | Report results | pass | pass | pass | Pass | pass | pass | pass |
| Assay | NLT 90.0% and NMT 115.0% of labeled amount of vancomycin | pass | pass | pass | Pass | pass | pass | pass |
| Impurity Compound 1 | No individual impurity is larger than 4.0% | pass | pass | pass | Pass | pass | pass | pass |
| Impurity Compound 2 | No individual impurity is larger than 4.0% | pass | pass | pass | Pass | pass | pass | pass |
| Largest individual impurity | No individual impurity is larger than 4.0% | pass | pass | pass | Pass | pass | pass | pass |
| Purity | NLT 88.0% | pass | pass | pass | Pass | pass | pass | pass |
| Particulate Matter | NMT 600 particles/mL @ >10 μm & NMT 6000 particles/mL @ >25 μm | pass | pass | pass | Pass | pass | pass | pass |

The results demonstrate that the concentrated vancomycin solution form of this invention is stable in the infusion fluids listed in package insert of the RLD when diluted and stored per the RLD package insert instructions. Furthermore, the results obtained indicated that the stability of the concentrated vancomycin solution F-82 is equivalent or better than that of the RLD. Neither the primary vancomycin impurities (CDP-1s) nor any other individual impurity equaled or exceeded the limit of 4.0% total area for any infusion fluid during the study. Therefore, the vancomycin solution compositions of this invention are compatible with and can be diluted using the same labeled infusion fluids that are permitted for use with the RLD.

EXAMPLE 9

The purpose of this study was to demonstrate the antibiotic activity (potency) of vancomycin in the solution compositions of the present invention. Antibiotic potency was determined using the current USP method for Antibiotic Assay <81>. The table below describes the vancomycin solution composition used to test antibiotic potency.

| % w/v | F-51 |
|---|---|
| Vancomycin | 1.0 |
| NaCl | 0.8 |
| L-tryptophan | 1.35 |
| Water | QS |
| pH | 4.7 +/- 0.1 |

The table below shows the results of antibiotic potency testing:

| Test | Bacterium strain | USP Specification | Day 1 (%) | Day 2 (%) | Day 3 (%) | Avg (%) |
|---|---|---|---|---|---|---|
| Vancomycin Assay per USP <81> | Bacillus subtilis ATCC633 | 90.0-115.0% | 102.9 | 105.4 | 111.0 | 106.4 |

The results demonstrate that the vancomycin solution formulations of the present invention passed the potency test and conforms to the USP specification for Antibiotic Assay.

EXAMPLE 10

The purpose of this study was to demonstrate the Minimum Inhibitory Concentration (MIC), the measure of the lowest level of an antibiotic agent that can inhibit microbial proliferation in liquid. Standards for this method are outlined by the Clinical and Laboratory Standards Institute (CLSI). The table below describes the vancomycin solution composition used to test antibiotic potency:

| % w/v | F-51 |
|---|---|
| Vancomycin | 1.0 |
| NaCl | 0.8 |
| L-tryptophan | 1.35 |
| Water | QS |
| pH | 4.7 +/- 0.3 |

The table below shows the results of antibiotic potency testing for F-51:

| Test | Bacteria strain | Specification | Replicate #1 (%) | Replicate #2 (%) | Avg (%) |
|---|---|---|---|---|---|
| MIC | E. faecalis ATCC 29212 | Report results | ≥0.1 | ≥0.1 | ≥0.1 |
| MIC | S. aureus ATCC 25923 | Report results | ≥0.1 | ≥0.1 | ≥0.1 |

The results demonstrate that the vancomycin solution composition of the present invention is sufficiently potent at least to a vancomycin concentration of 0.001% w/v.

EXAMPLE 11

The purpose of this study was to demonstrate the Minimum Inhibitory Concentration (MIC), the measure of the lowest level of an antibiotic agent that can inhibit microbial proliferation in liquid. Standards for this method are outlined by the Clinical and Laboratory Standards Institute (CLSI).

The table below describes the vancomycin solution composition used to test antibiotic potency.

| % w/v | F-51 | Reference Solution |
|---|---|---|
| Vancomycin | 1.0 | 1.0 |
| NaCl | 0.8 | — |
| L-tryptophan | 1.35 | — |
| Water | QS | QS |
| pH | 4.7 +/- 0.1 | 4.7 +/- 0.1 |

The table below describes the testing parameters used in this study.

| Parameter | Value | Parameter | Value |
|---|---|---|---|
| Concentrations | 50 to 0.1% | Culture growth time | 18-24 hours |
| Replicates | 2 | Test dilution media | Mueller Hinton broth |
| Bacteria | E. faecalis, S. aureus | Inoculum volume | 0.100 mL |
| Culture growth media | Tryptic soy broth | Incubation time | 24 hours |
| Culture dilution media | Mueller Hinton broth | Enumeration plate incubation time | 24-48 hours |
| Inoculum concentration | 1.0 x 104 CFU/well | Enumeration plate incubation temperature | 36 +/- 1° C. |
| Incubation temperature | 36 +/- 1° C. | Final well volumes | 0.200 mL |

The table below shows the results of antibiotic potency testing:

| Sample | Test | Bacteria strain | Specification | Replicate #1 (%) | Replicate #2 (%) | Avg (%) |
|---|---|---|---|---|---|---|
| F-51 | MIC | E. faecalis ATCC 29212 | Report results | >0.1 | >0.1 | >0.1 |
| Reference Solution - a vancomycin Solution without tryptophan | MIC | E. faecalis ATCC 29212 | Report results | >0.1 | >0.1 | >0.1 |
| F-51 | MIC | S. aureus ATCC 25923 | Report results | >0.1 | >0.1 | >0.1 |
| Reference Solution - a vancomycin solution without tryptophan | MIC | S. aureus ATCC 25923 | Report results | >0.1 | >0.1 | >0.1 |

The results demonstrate that addition of tryptophan to the vancomycin solution of the present invention does not affect the MIC of vancomycin for the tested bacterial strains.

EXAMPLE 12

The purpose of this study was to demonstrate the stability of tryptophan in the vancomycin solution of the present invention. The table below describes the vancomycin solution and corresponding vehicle solution composition used to test tryptophan stability.

| % w/v | F-50 | F-50 Vehicle |
|---|---|---|
| Vancomycin | 1.0 | — |
| NaCl | 0.8 | 0.8 |
| L-tryptophan | 1.5 | 1.5 |
| Water | QS | QS |
| pH | 4.7 +/− 0.1 | 4.7 +/− 0.1 |

The table below the storage/stress conditions used to evaluate tryptophan stability.

| # | Sample | Sample treatment/ storage condition prior to test |
|---|---|---|
| 1 | F-50 | 2-8° C. x 6 months |
| 2 | F-50 | 2-8° C. x 6 months |
| 3 | Vehicle | 2-8° C. x 6 M + 60° C. for 24 hr |
| 4 | | 2-8° C. x 6 M + 121° C. for 15 min (autoclave) |

The table below summarizes the peak area (%) of the tryptophan-related impurities or degradation products. Vancomycin and its related peaks are not included in the HPLC data integration and calculation.

| # | ID | Sample treatment/ storage condition prior to test | Tryptophan (% peak area) | # of impurity peak > 0.1% of total peak area | Comment |
|---|---|---|---|---|---|
| 1 | F-50 | 2-8° C. x 6 months | 99.97 | 0 | No tryptophan-related impurity exceeds to 0.1% or the "Reporting Threshold" |
| 2 | F-50 vehicle | 2-8° C. x 6 months | 99.97 | 0 | |
| 3 | F-50 vehicle | 2-8° C. x 6 M + 60° C. for 24 hr | 99.89 | 0 | |
| 4 | F-50 vehicle | 2-8° C. x 6 M + 121° C. for 15 min (autoclave) | 99.52 | 0 | |

The results demonstrate that tryptophan is very stable in the vancomycin solution of the present invention and no impurity or degradation products are of concern. There is no tryptophan-related impurity with peak area exceeding 0.1% found in the 2-8° C.×6 months vancomycin solution and its vehicle. Even after a substantial stress such as autoclaving, the tryptophan-related impurities formed in the vancomycin solution remained below 0.1% or the "Reporting Threshold" according to the FDA's impurity guidance (Guidance for Industry Q3B(R2) Impurities in New Drug Products). Tryptophan purity is expected to remain above 99.9% by peak area. No tryptophan impurities are expected to interfere with known vancomycin impurities by the HPLC method.

Modifications and variations of the present invention will be obvious to those skilled in the art from the foregoing detailed description and are intended to fall within the scope of the following claims. The teachings of all references cited herein are specifically incorporated by reference.

I claim:

1. A clear and injectable solution composition, said solution composition comprising:
   (a) a glycopeptide selected from the group consisting of vancomycin having an empirical formula of $C_{66}H_{75}Cl_2N_9O_{24}$, norvancomycin or salts thereof, at a concentration of about 0.1% w/v to about 12% w/v;
   (b) tryptophan having an empirical formula of $C_{11}H_{12}N_2O_2$ selected from the group consisting of the L-form, the D-form, a mixture of the L- and D-forms or salts thereof, at a concentration between about 0.1% w/v to 2.5% w/v, wherein tryptophan inhibits formation of crystalline degradation product-1 (CDP-1);
   (c) water, wherein the pH of the solution composition is between about 3 to about 6; and CDP-1 is no more than 4% based on high performance liquid chromatography (HPLC) peak area after storage at 2-8° C. for 20 months.

2. The composition of claim 1, wherein about 0.1% w/v to about 10% w/v vancomycin is present in the composition.

3. The composition of claim 1, wherein vancomycin is present at about 0.5% w/v to about 5% w/v in the composition.

4. The composition of claim 1, wherein the vancomycin salt is vancomycin hydrochloride salt.

5. The composition of claim 1, wherein the composition further comprises a preservative.

6. The composition of claim 5, wherein the preservative is selected from the group consisting of cresols, phenol, benzyl alcohol, ethanol, chlorobutanol, parabens, imidura, benzalkonium chloride, ethylenediaminetetraacetic acid (EDTA) or its salt, and a combination thereof.

7. The composition of claim 1, comprising:
   (a) vancomycin hydrochloride at about 0.1 w/v to 12% w/v;
   (b) tryptophan at about 0.1 w/v to 2.5% w/v; and
   (c) water, wherein the composition has a pH of between 3.5 to 6.

8. The composition of claim 1, comprising:
   (a) vancomycin hydrochloride at about 0.5% w/v;
   (b) tryptophan at about 0.3 w/v to 1.5% w/v; and
   (c) water, wherein the composition has a pH of between 3.5 to 5.

9. The composition of claim 1, comprising:
   (a) vancomycin hydrochloride at about 1% w/v;
   (b) tryptophan at about 0.3 w/v to 1.5% w/v; and
   (c) water, wherein the composition has a pH of between 3.5 to 5.

10. The composition of claim 1, comprising:
(a) vancomycin hydrochloride at about 5% w/v;
(b) tryptophan at about 0.3 w/v to 1.5% w/v; and
(c) water, wherein the composition has a pH of between 3.5 to 5.

11. The composition of claim 1, wherein said composition is administered to a human or animal subject by oral administration, injection through a needle, instillation through a catheter, or applications onto the skin, mucous membranes, in wounds, into the eyes, ears, vagina, urethra or rectum.

12. A method for treating infections caused by microorganisms that are susceptible to vancomycin or for prophylaxis treatment, the method comprising
administering a solution composition of claim 1,
to thereby treat the infection.

13. The method of claim 12, wherein said method comprises administering a solution composition wherein vancomycin is present at about 0.5% w/v to about 5% w/v in the composition.

14. A method for preparing a solution composition of claim 1, said method comprising: dissolving in water the following components in any order:
(a) a glycopeptide selected from the group consisting of vancomycin having an empirical formula of $C_{66}H_{75}C_2N_9O_{24}$, norvancomycin or salts thereof, at a concentration of about 0.1% w/v to about 12% w/v;
(b) tryptophan having an empirical formula of $C_{11}H_{12}N_2O_2$ selected from the group consisting of the L-form, the D-form, a mixture of the L- and D-forms or salts thereof, at a concentration between about 0.1% w/v to 2.5% w/v; and
(c) sodium chloride as needed to achieve an isotonic concentration.

15. The method of claim 14, wherein said method comprises dissolving a lyophilized dry powder or a solid composition in water to form a clear solution of:
(a) vancomycin at a concentration of about 0.1 w/v to 12% w/v; and
(b) tryptophan to a concentration of about 0.1 w/v to 2.5% w/v.

* * * * *